(12) United States Patent
Hwang et al.

(10) Patent No.: US 11,473,079 B2
(45) Date of Patent: Oct. 18, 2022

(54) METHOD FOR PRENATAL DIAGNOSIS USING DIGITAL PCR

(71) Applicant: Biocore Co., Ltd., Seoul (KR)

(72) Inventors: Seung Yong Hwang, Seoul (KR); Moon Ju Oh, Seoul (KR); Seung Jun Kim, Gyeonggi-do (KR); Jong Pil Youn, Gyeonggi-do (KR); Ji Hoon Kim, Gyeonggi-do (KR); Seung Yong Lee, Gyeonggi-do (KR); Jeong Jin Ahn, Seoul (KR); Joon Soo Park, Seoul (KR); Hyo Jung Choi, Gyeonggi-do (KR)

(73) Assignee: BIOCORE CO., LTD., Seoul (KR)

( * ) Notice: Subject to any disclaimer, the term of this patent is extended or adjusted under 35 U.S.C. 154(b) by 426 days.

(21) Appl. No.: 15/770,988

(22) PCT Filed: Oct. 28, 2016

(86) PCT No.: PCT/KR2016/012236
§ 371 (c)(1),
(2) Date: Apr. 25, 2018

(87) PCT Pub. No.: WO2017/074094
PCT Pub. Date: May 4, 2017

(65) Prior Publication Data
US 2019/0100749 A1 Apr. 4, 2019

(30) Foreign Application Priority Data

Oct. 29, 2015 (KR) .................. 10-2015-0151313
Oct. 14, 2016 (KR) .................. 10-2016-0133529

(51) Int. Cl.
C12Q 1/686 (2018.01)
C12Q 1/6827 (2018.01)
C12Q 1/6806 (2018.01)
C12N 15/10 (2006.01)

(52) U.S. Cl.
CPC ......... *C12N 15/1013* (2013.01); *C12Q 1/686* (2013.01); *C12Q 1/6806* (2013.01); *C12Q 1/6827* (2013.01); *C12Q 2600/112* (2013.01); *C12Q 2600/16* (2013.01); *C12Q 2600/166* (2013.01)

(58) Field of Classification Search
CPC .................. C12N 15/1013; C12Q 1/6827
See application file for complete search history.

(56) References Cited

U.S. PATENT DOCUMENTS

| | | | |
|---|---|---|---|
| 6,534,262 B1 * | 3/2003 | McKernan | C12N 15/1006 435/6.16 |
| 9,892,230 B2 * | 2/2018 | Lo | C12Q 1/6809 |
| 2009/0053719 A1 | 2/2009 | Lo et al. | |
| 2009/0087847 A1 * | 4/2009 | Lo | C12Q 1/6888 435/6.12 |
| 2010/0255493 A1 | 10/2010 | Quake | |
| 2010/0256013 A1 | 10/2010 | Quake et al. | |
| 2011/0039724 A1 * | 2/2011 | Lo | C12Q 1/6827 506/9 |
| 2011/0151442 A1 | 6/2011 | Fan et al. | |
| 2012/0183963 A1 | 7/2012 | Stoughton et al. | |
| 2012/0208708 A1 * | 8/2012 | Lo | C12Q 1/6883 506/2 |
| 2013/0085681 A1 * | 4/2013 | Deciu | C12Q 1/6827 702/19 |
| 2013/0295565 A1 | 11/2013 | Shoemaker | |
| 2014/0186827 A1 | 7/2014 | Pieprzyk et al. | |

FOREIGN PATENT DOCUMENTS

| | | |
|---|---|---|
| GB | 2485850 A | 5/2012 |
| KR | 10-1387582 | 5/2013 |
| KR | 20140140122 A | 12/2014 |
| KR | 20150067161 A1 | 6/2015 |
| WO | 2009019455 A2 | 2/2009 |

OTHER PUBLICATIONS

Yaha-Graison, Classification of Human Chromosome 21 Gene-Expression Variations in Down Syndrome: Impact on Disease Phenotypes, Am J Hum Genet, 81(3): 475-491, doi: 10/1086/520000, 2007. (Year: 2007).*
Lowe, A computer program for selection of oligonucleotide primers for polymerase chain reactions, Nucleic Acids Research, 18(7): 1757-1761, 1990. (Year: 1990).*
GenBank Accession No. NG_011402.2 (Year: 2020).*
GenBank Accession No. NM_002871.5 (Year: 2020).*
Wilcox, Mutations in the Gene Encoding Tight Junction Claudin-14 Cause Autosomal Recessive Deafness DFNB29, Cell, 104: 165-172, 2001. (Year: 2011).*
GenBank Accession No. NM_001286789.2 (Year: 2020).*
GenBank Accession No. NG_052982.1 (Year: 2020).*
GenBank Accession No. NG_011777.1 (Year: 2020).*

(Continued)

*Primary Examiner* — Samuel C Woolwine
*Assistant Examiner* — Carolyn L Greene
(74) *Attorney, Agent, or Firm* — DLA Piper LLP US

(57) ABSTRACT

The present invention relates to a method for prenatal diagnosis using digital PCR, and more particularly to a method for providing information for diagnosis of chromosomal aneuploidy in a fetus, comprising: (a) extracting DNAs from pregnant woman's blood; (b) classifying the DNAs according to size to obtain DNAs having a size of 1,000 bp or less; (c) performing digital PCR using the obtained DNAs of step (b), for a control gene located on a chromosome not associated with chromosomal aneuploidy and a target gene located on a chromosome associated with chromosomal aneuploidy; (d) calculating a ratio of a quantitative digital PCR value of the target gene to a quantitative digital PCR value of the control gene; and (e) determining that when the ratio calculated in step (d) is 0.70-1.14, a chromosome number of the fetus is normal.

15 Claims, 5 Drawing Sheets

Specification includes a Sequence Listing.

(56) References Cited

OTHER PUBLICATIONS

GenBank Accession No. AC104695.2 (Year: 2005).*
Beckman Coulter Inc., "SPRIselect User Guide", Oct. 2012.
Bernhard et al, "Digital PCR: a powerful new tool for noninvasive prenatal diagnosis?", Prenatal Diagnosis, vol. 28, pp. 1087-1093, (2008).
Su et al, "Removal of High-Molecular-Weight DNA by Carboxylated Magnetic Beads Enhances the Detection of Mutated K-ras DNA in Urine", Ann. NY Acad. Sci., vol. 1137, pp. 82-91, (2008).
Li et al, "Size Separation of Circulatory DNA in Maternal Plasma Permits Ready Detection of Fetal DNA Polymorhisms", Clinical Chemistry, vol. 50, No. 6, pp. 1002-1011, (2004).
Hahn et al, "Micosystems for Isolation of Fetal DNA from Maternal Plasma by Preparative Size Separation", Clinical Chemistry, vol. 25, No. 12, pp. 2144-2152, (2009).
European Application No. 16860277.9-1118 / 3368690, Extended European Search Report dated Mar. 8, 2019, 9 pages.
Fan et al., "Microfluidic digital PCR enables rapid prenatal diagnosis of fetal aneuploidy", American Journal of Obstetrics and Gynecology, 200(5):543 (2009).
Yu et al., "Size-based molecular diagnostics using plasma DNA for noninvasive prenatal testing", PNAS, 111(23):8583-8588 (2014).
Chan et al., "Size distributions of maternal and fetal DNA in maternal", Clinical Chemistry, 50(1):88-92 (2004).

* cited by examiner

[FIG. 2]

| | Normal gDNA | | | | | | | |
|---|---|---|---|---|---|---|---|---|
| | 01_06+ 02_06(F) | 02_06(F) | 21(V) | Ratio | | Average (probe) | Average (Chr21) | Risk |
| | | | | Chr1 | Chr2 | | | |
| #1 | 7.2 | 4.2 | 4.1 | 1.3667 | 0.9762 | 1.1714 | 1.08 | Low Risk |
| #2 | 7.8 | 3.9 | 4 | 1.0256 | 1.0256 | 1.0256 | | |
| #3 | 9.8 | 4.8 | 5.3 | 1.0600 | 1.1042 | 1.0821 | | |
| #4 | 11.8 | 4.7 | 5.8 | 0.8169 | 1.2340 | 1.0255 | | |

| | T21 gDNA | | | | | | | |
|---|---|---|---|---|---|---|---|---|
| | 01_06+ 02_06(F) | 02_06(F) | 21(V) | Ratio | | Average (probe) | Average (Chr21) | Risk |
| | | | | Chr1 | Chr2 | | | |
| #1 | 2.7 | 1.5 | 2.8 | 2.3333 | 1.8667 | 2.1000 | 1.51 | High Risk |
| #2 | 3.1 | 1.37 | 2.2 | 1.2717 | 1.6058 | 1.4388 | | |
| #3 | 4 | 1.7 | 2.7 | 1.1739 | 1.5882 | 1.3811 | | |
| #4 | 4.5 | 2.6 | 2.5 | 1.3158 | 0.9615 | 1.1387 | | |

[FIG. 3]

| | cfDNA(Amniotic fluid)_N | | | | | | | |
|---|---|---|---|---|---|---|---|---|
| | 01_06+ 02_06(F) | 02_06(F) | 21(V) | Ratio | | Average (probe) | Average (Chr21) | Risk |
| | | | | Chr1 | Chr2 | | | |
| #1 | 34 | 18.1 | 20.3 | 1.2767 | 1.1215 | 1.1991 | 1.05 | Low Risk |
| #2 | 36.5 | 20.1 | 19.1 | 1.1646 | 0.9502 | 1.0574 | | |
| #3 | 33 | 16.9 | 16.5 | 1.0248 | 0.9763 | 1.0006 | | |
| #4 | 34.1 | 17 | 16.3 | 0.9532 | 0.9588 | 0.9560 | | |

| | cfDNA(Amniotic fluid)_T21 | | | | | | | |
|---|---|---|---|---|---|---|---|---|
| | 01_06+ 02_06(F) | 02_06(F) | 21(V) | Ratio | | Average (probe) | Average (Chr21) | Risk |
| | | | | Chr1 | Chr2 | | | |
| #1 | 32.4 | 17 | 26.8 | 1.7403 | 1.5765 | 1.6584 | 1.59 | High Risk |
| #2 | 34.8 | 17.4 | 29.5 | 1.6954 | 1.6954 | 1.6954 | | |
| #3 | 34.5 | 18.2 | 25.6 | 1.5706 | 1.4066 | 1.4886 | | |
| #4 | 33.1 | 16 | 24.9 | 1.4561 | 1.5563 | 1.5062 | | |

[FIG. 4]
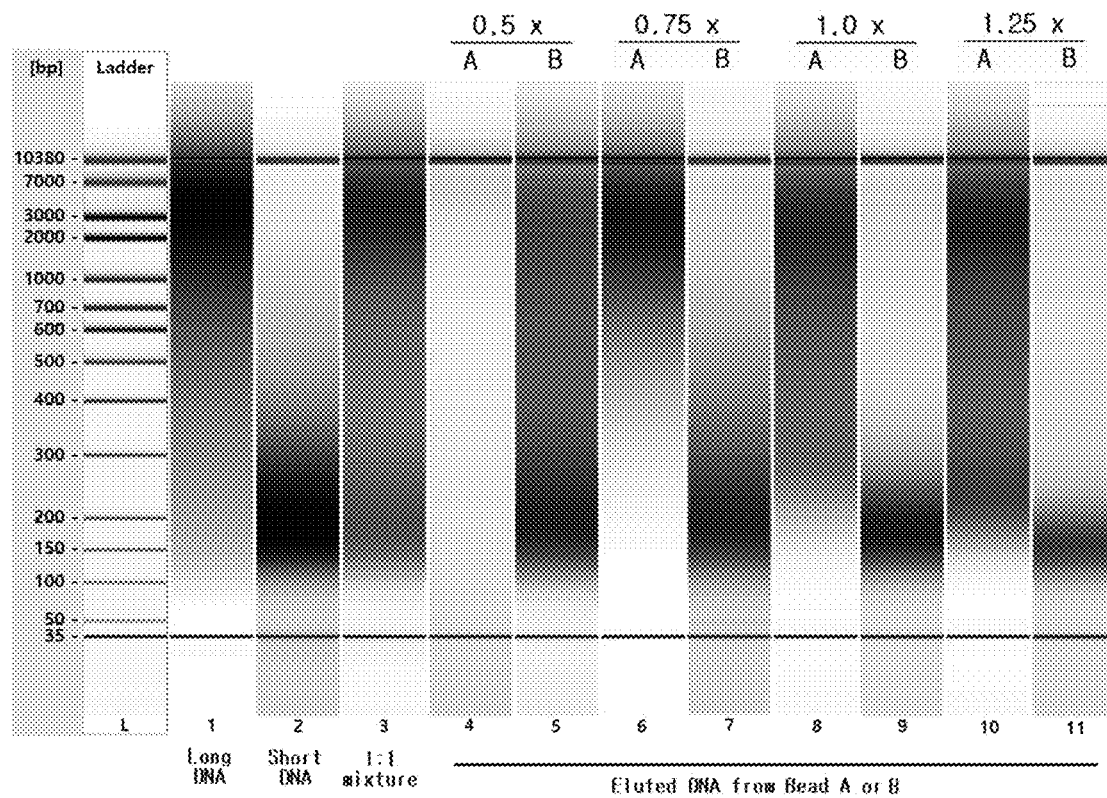
[FIG. 5]
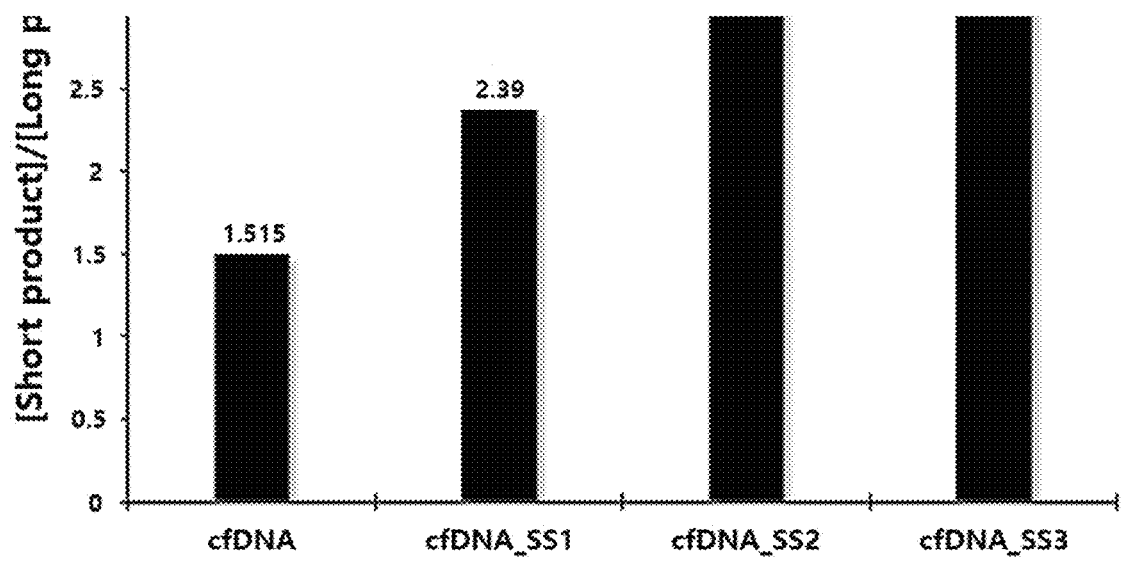

[FIG. 6]
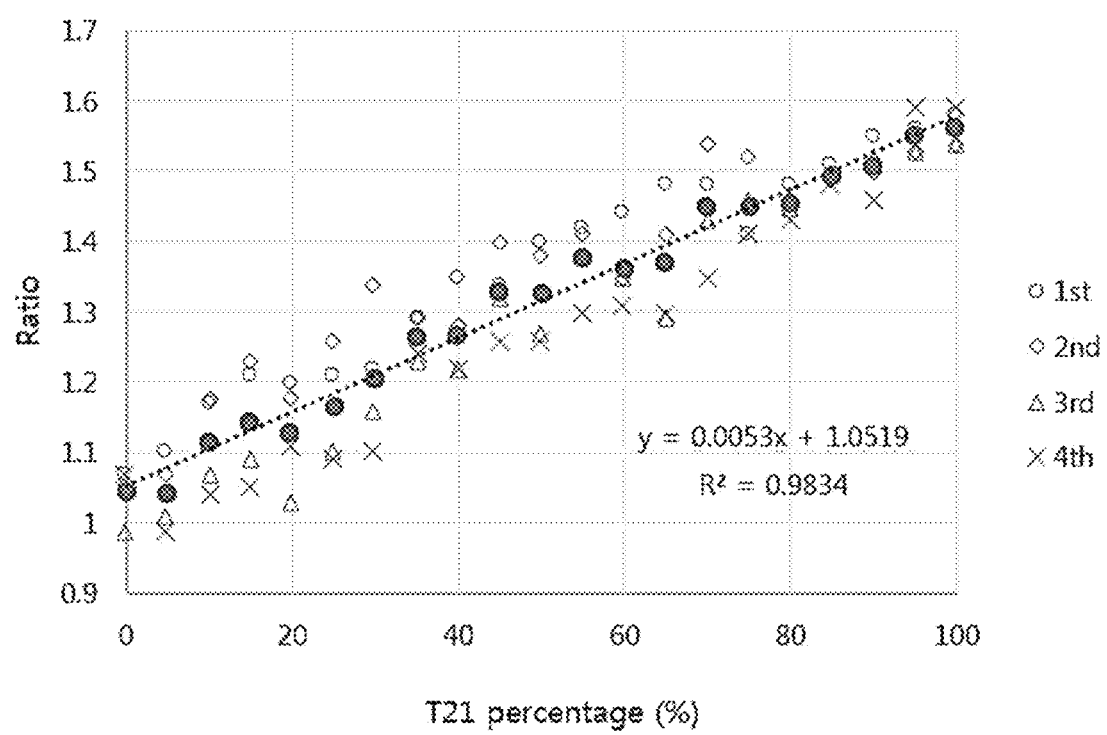

[FIG. 7]

| | | | | | | | |
|---|---|---|---|---|---|---|---|
| | colspan="7" | cfDNA(Plasma)_N_1 | | | | | |
| | 01_06+ 02_06(F) | 02_06(F) | 21(V) | Ratio Chr1 | Ratio Chr2 | Average (probe) | Average (Chr21) | Risk |
| #1 | 3.6 | 1.7 | 1.9 | 1.0000 | 1.1176 | 1.0588 | 1.04 | Low Risk |
| #2 | 3.5 | 1.6 | 1.6 | 0.8421 | 1.0000 | 0.9211 | | |
| #3 | 5 | 2.3 | 2.5 | 0.9259 | 1.0870 | 1.0064 | | |
| #4 | 4.5 | 1.7 | 2.5 | 0.8929 | 1.4706 | 1.1817 | | |

| | | | | | | | |
|---|---|---|---|---|---|---|---|
| | colspan="7" | cfDNA(Plasma)_N_2 | | | | | |
| | 01_06+ 02_06(F) | 02_06(F) | 21(V) | Ratio Chr1 | Ratio Chr2 | Average (probe) | Average (Chr21) | Risk |
| #1 | 8.9 | 4.7 | 3.9 | 0.9286 | 0.8298 | 0.8792 | 1.08 | Low Risk |
| #2 | 9.6 | 4.9 | 4.1 | 0.8723 | 0.8367 | 0.8545 | | |
| #3 | 7.1 | 3.9 | 5.3 | 1.6563 | 1.3590 | 1.5076 | | |
| #4 | 8.4 | 4.3 | 4.6 | 1.1220 | 1.0698 | 1.0959 | | |

| | | | | | | | |
|---|---|---|---|---|---|---|---|
| | colspan="7" | cfDNA(Plasma)_N_3 | | | | | |
| | 01_06+ 02_06(F) | 02_06(F) | 21(V) | Ratio Chr1 | Ratio Chr2 | Average (probe) | Average (Chr21) | Risk |
| #1 | 13 | 7.3 | 4.8 | 0.8421 | 0.6575 | 0.7498 | 0.98 | Low Risk |
| #2 | 10.6 | 6.7 | 4.7 | 1.2051 | 0.7015 | 0.9533 | | |
| #3 | 12.2 | 7.6 | 5 | 1.0870 | 0.6579 | 0.8724 | | |
| #4 | 10.5 | 6.4 | 6.8 | 1.6585 | 1.0625 | 1.3605 | | |

| | | | | | | | |
|---|---|---|---|---|---|---|---|
| | colspan="7" | cfDNA(Plasma)_T21_1 | | | | | |
| | 01_06+ 02_06(F) | 02_06(F) | 21(V) | Ratio Chr1 | Ratio Chr2 | Average (probe) | Average (Chr21) | Risk |
| #1 | 3.6 | 1.6 | 2.7 | 1.3500 | 1.6875 | 1.5188 | 1.31 | High Risk |
| #2 | 2.8 | 1.2 | 1.7 | 1.2143 | 1.4167 | 1.3155 | | |
| #3 | 2.7 | 1.2 | 1.7 | 1.1933 | 1.4167 | 1.2750 | | |
| #4 | 3.6 | 1.8 | 2 | 1.1111 | 1.1111 | 1.1111 | | |

| | | | | | | | |
|---|---|---|---|---|---|---|---|
| | colspan="7" | cfDNA(Plasma)_T21_2 | | | | | |
| | 01_06+ 02_06(F) | 02_06(F) | 21(V) | Ratio Chr1 | Ratio Chr2 | Average (probe) | Average (Chr21) | Risk |
| #1 | 9.3 | 5 | 4.3 | 1.0000 | 0.8600 | 0.9300 | 1.15 | High Risk |
| #2 | 10.8 | 5.6 | 7.6 | 1.4615 | 1.3571 | 1.4093 | | |
| #3 | 9.1 | 3.8 | 5.3 | 1.0000 | 1.3947 | 1.1974 | | |
| #4 | 9.8 | 5 | 5.2 | 1.0833 | 1.0400 | 1.0617 | | |

| | | | | | | | |
|---|---|---|---|---|---|---|---|
| | colspan="7" | cfDNA(Plasma)_T21_3 | | | | | |
| | 01_06+ 02_06(F) | 02_06(F) | 21(V) | Ratio Chr1 | Ratio Chr2 | Average (probe) | Average (Chr21) | Risk |
| #1 | 3.8 | 2 | 2.4 | 1.3333 | 1.2000 | 1.2667 | 1.15 | High Risk |
| #2 | 3.2 | 1.4 | 1.6 | 0.8889 | 1.1429 | 1.0159 | | |
| #3 | 3.2 | 1.4 | 1.6 | 0.8889 | 1.1429 | 1.0159 | | |
| #4 | 2.5 | 1.4 | 1.6 | 1.4545 | 1.1429 | 1.2987 | | |

SEQUENCE LISTING

<160> NUMBER OF SEQ ID NOS: 36

<210> SEQ ID NO 1
<211> LENGTH: 165
<212> TYPE: DNA
<213> ORGANISM: Homo sapiens

<400> SEQUENCE: 1
ctgcagttct ttgtgaacac tctcatttgt tgtatctgta ggctgtctct ctcagtggta      60
aatgccttcg tgtgtttgta atgctgatgg ttacttgagg taaataagaa tgtaccactt     120
ggctcagtgt gcatgatgta agcttgtctt tgttgtatgt tggct                     165

<210> SEQ ID NO 2
<211> LENGTH: 161
<212> TYPE: DNA
<213> ORGANISM: Homo sapiens

<400> SEQUENCE: 2
tgactatcac atgtctttgg ttgtaaactg ctgtgatagt taccctaagt aatgggacag      60
gagatgaacc cacccattaa ataacacagc aattaagcag ccacttttag aaaaatttaa    120
atgtgtggct tcgagttggg tacttgcatg tacagcttac t                         161

<210> SEQ ID NO 3
<211> LENGTH: 118
<212> TYPE: DNA
<213> ORGANISM: Homo sapiens

<400> SEQUENCE: 3
cccaggctat gctagaaggt atgcttacaa ttggaaaagt gtaggcagat aacattaaat      60
ggcaatagca tgtgtaaact aactgcaaat gaggaaaagg acattctaaa gacaggat       118

<210> SEQ ID NO 4
<211> LENGTH: 110
<212> TYPE: DNA
<213> ORGANISM: Homo sapiens

<400> SEQUENCE: 4
ggaccagagg tttattggag gtctaaatat ttatggagag caatgatggc taattttaga      60
aaccattagg ttgctatttt taaacgtgtg ctataaggat ttgctaattt                110

<210> SEQ ID NO 5
<211> LENGTH: 127
<212> TYPE: DNA
<213> ORGANISM: Homo sapiens

<400> SEQUENCE: 5
gaggaagcaa ctagaaaaca atggaaggga cttcagatgg taaggtttct gtttagtact      60
tatttcaatt ttaggcctcc tgaatagtag aggtggtgac aggaggatac ctgaaacctt    120

```
ggttata                                                                         127

<210> SEQ ID NO 6
<211> LENGTH: 112
<212> TYPE: DNA
<213> ORGANISM: Homo sapiens

<400> SEQUENCE: 6
gggaacatcc caggttcagt aaaaatacag agtatttgcg ttaaactgga cctcagtggg      60
gatgtgatgg gaggtatgag acagattgtg cccttatcct tttctcttct tg            112

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
cgtgtgtttg taatgctgat ggt                                              23

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
catcatgcac actgagccaa gt                                               22

<210> SEQ ID NO 9
<211> LENGTH: 23
<212> TYPE: DNA
<213> ORGANISM: Artificial Sequence
<220> FEATURE:
<223> OTHER INFORMATION: Probe

<400> SEQUENCE: 9
acttgaggta aataagaatg tac                                              23

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
ccctaagtaa tgggacagga gatg                                             24

<210> SEQ ID NO 11
<211> LENGTH: 23
<212> TYPE: DNA
<213> ORGANISM: Artificial Sequence
<220> FEATURE:
<223> OTHER INFORMATION: Primer

<400> SEQUENCE: 11
aagtggctgc ttaattgctg tgt                                              23

<210> SEQ ID NO 12
<211> LENGTH: 15
<212> TYPE: DNA
```

```
<213> ORGANISM: Artificial Sequence
<220> FEATURE:
<223> OTHER INFORMATION: Probe

<400> SEQUENCE: 12
acccacccat taaat                                                    15

<210> SEQ ID NO 13
<211> LENGTH: 26
<212> TYPE: DNA
<213> ORGANISM: Artificial Sequence
<220> FEATURE:
<223> OTHER INFORMATION: Primer

<400> SEQUENCE: 13
tgctagaagg tatgcttaca attgga                                        26

<210> SEQ ID NO 14
<211> LENGTH: 26
<212> TYPE: DNA
<213> ORGANISM: Artificial Sequence
<220> FEATURE:
<223> OTHER INFORMATION: Primer

<400> SEQUENCE: 14
tcatttgcag ttagtttaca catgct                                        26

<210> SEQ ID NO 15
<211> LENGTH: 17
<212> TYPE: DNA
<213> ORGANISM: Artificial Sequence
<220> FEATURE:
<223> OTHER INFORMATION: Probe

<400> SEQUENCE: 15
aagtgtaggc agataac                                                  17

<210> SEQ ID NO 16
<211> LENGTH: 27
<212> TYPE: DNA
<213> ORGANISM: Artificial Sequence
<220> FEATURE:
<223> OTHER INFORMATION: Primer

<400> SEQUENCE: 16
gaccagaggt ttattggagg tctaaat                                       27

<210> SEQ ID NO 17
<211> LENGTH: 26
<212> TYPE: DNA
<213> ORGANISM: Artificial Sequence
<220> FEATURE:
<223> OTHER INFORMATION: Primer

<400> SEQUENCE: 17
cacgtttaaa aatagcaacc taatgg                                        26

<210> SEQ ID NO 18
<211> LENGTH: 18
<212> TYPE: DNA
<213> ORGANISM: Artificial Sequence
<220> FEATURE:
<223> OTHER INFORMATION: Probe

<400> SEQUENCE: 18
tttatggaga gcaatgat                                                 18
```

```
<210> SEQ ID NO 19
<211> LENGTH: 26
<212> TYPE: DNA
<213> ORGANISM: Artificial Sequence
<220> FEATURE:
<223> OTHER INFORMATION: Primer

<400> SEQUENCE: 19
caactagaaa acaatggaag ggactt                                          26

<210> SEQ ID NO 20
<211> LENGTH: 25
<212> TYPE: DNA
<213> ORGANISM: Artificial Sequence
<220> FEATURE:
<223> OTHER INFORMATION: Primer

<400> SEQUENCE: 20
tcaggaggcc taaaattgaa ataag                                           25

<210> SEQ ID NO 21
<211> LENGTH: 22
<212> TYPE: DNA
<213> ORGANISM: Artificial Sequence
<220> FEATURE:
<223> OTHER INFORMATION: Probe

<400> SEQUENCE: 21
agatggtaag gtttctgttt ag                                              22

<210> SEQ ID NO 22
<211> LENGTH: 26
<212> TYPE: DNA
<213> ORGANISM: Artificial Sequence
<220> FEATURE:
<223> OTHER INFORMATION: Primer

<400> SEQUENCE: 22
catcccaggt tcagtaaaaa tacaga                                          26

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
ctgtctcata cctcccatca catc                                            24

<210> SEQ ID NO 24
<211> LENGTH: 20
<212> TYPE: DNA
<213> ORGANISM: Artificial Sequence
<220> FEATURE:
<223> OTHER INFORMATION: Probe

<400> SEQUENCE: 24
tatttgcgtt aaactggacc                                                 20

<210> SEQ ID NO 25
<211> LENGTH: 18
<212> TYPE: DNA
<213> ORGANISM: Artificial Sequence
<220> FEATURE:
```

<223> OTHER INFORMATION: Primer

<400> SEQUENCE: 25
tcaggttgac gccgctgt                                         18

<210> SEQ ID NO 26
<211> LENGTH: 19
<212> TYPE: DNA
<213> ORGANISM: Artificial Sequence
<220> FEATURE:
<223> OTHER INFORMATION: Primer

<400> SEQUENCE: 26
ttcgtagccg ttctgctgc                                        19

<210> SEQ ID NO 27
<211> LENGTH: 26
<212> TYPE: DNA
<213> ORGANISM: Artificial Sequence
<220> FEATURE:
<223> OTHER INFORMATION: Primer

<400> SEQUENCE: 27
tctataaatg gacaccgatg ggtagt                                26

<210> SEQ ID NO 28
<211> LENGTH: 21
<212> TYPE: DNA
<213> ORGANISM: Artificial Sequence
<220> FEATURE:
<223> OTHER INFORMATION: Probe

<400> SEQUENCE: 28
accccagagg agcgccacct g                                     21

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
tacaggaagt cccttgccat                                       20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
cctgtgtgga cttgggagag                                       20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
cacgaaggct catcattcaa                                       20

```
<210> SEQ ID NO 32
<211> LENGTH: 27
<212> TYPE: DNA
<213> ORGANISM: Artificial Sequence
<220> FEATURE:
<223> OTHER INFORMATION: Probe

<400> SEQUENCE: 32
cccacttctc tctaaggaga atggccc                                         27

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
agagctacga gctgcctgac                                                 20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
ccatctcttg ctcgaagtcc                                                 20

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
ggcaggactt agcttccaca                                                 20

<210> SEQ ID NO 36
<211> LENGTH: 20
<212> TYPE: DNA
<213> ORGANISM: Artificial Sequence
<220> FEATURE:
<223> OTHER INFORMATION: Probe

<400> SEQUENCE: 36
ttccgctgcc ctgaggcact                                                 20
```

METHOD FOR PRENATAL DIAGNOSIS USING DIGITAL PCR

TECHNICAL FIELD

The present invention relates to a method for prenatal diagnosis using digital PCR.

SEQUENCE LISTING

The instant application contains a Sequence Listing which has been submitted in ASCII format via EFS-Web and is hereby incorporated by reference in its entirety. Said ASCII copy, created on Sep. 11, 2018, is named 18_546WOUS_CorrectiveSeqListing_ST25.txt and is 7,030 bytes in size.

BACKGROUND ART

Due to causes such as an increase in marriage age and an increase in women's childbearing age, the likelihood of development of fetal genetic diseases has recently increased rapidly for 10 years. If diseases, including fetal genetic diseases, are detected in the early stage of pregnancy, early medical measures required for safety are possible while the pain of pregnant women and fetuses is reduced. Thus, early diagnosis of fetal genetic abnormalities is very important. Genetic abnormalities that can occur in fetuses include partial chromosomal translocation, deletion, duplication, insertion and numerical abnormalities (for example, trisomy). When such chromosomal abnormalities are present, structural abnormalities and functional abnormalities occur throughout the fetal body. Particularly, it is known that chromosomal numerical abnormalities occur with a higher frequency in older pregnant women.

In general, amniocentesis is used to diagnose fetal genetic abnormalities. However, amniocentesis is an invasive testing method, can cause various problems, including bacterial infection of the amnion by syringes, wounds caused by syringes, and amniotic fluid leakage, and can also cause abortion in severe cases. For this reason, in recent years, methods of diagnosing fetal genetic abnormalities by extracting fetal DNA from the blood of pregnant women have been introduced. However, the amount of fetal DNA contained in the blood of pregnant women is very smaller than that pregnant woman's DNA, and thus analysis of fetal genetic information has a very low accuracy. In connection with this, Korean Patent No. 10-1387582 discloses a method capable of detecting cell-free fetal nucleic acids in pregnant women by performing real-time PCR that targets a very small amount of cell-free fetal nucleic acids present in pregnant woman's blood. Real-time PCR is a non-invasive method, but has disadvantages in that performing a variety of tests at the same time is limited, the use of a standard curve is required for accurate detection of fetal genetic abnormalities, and a certain amount or more of a sample is required.

Accordingly, the present invention has been made in order to solve the above-described problems occurring in the prior art, and is intended to a method capable of increasing the accuracy of analysis of fetal genetic information by concentrating fetal DNA when prenatal diagnosis is performed using pregnant woman's blood. The prenatal diagnosis method of the present invention is safe for all pregnant women and fetuses, convenient, accurate and reliable, and thus is expected to be highly useful in the prenatal diagnosis field.

DISCLOSURE OF INVENTION

Technical Problem

The present invention has been made in order to solve the above-described problems occurring in the prior art, and is directed to a method for prenatal diagnosis using digital PCR.

However, the technical object to be achieved by the present invention is not limited to the above technical object, and other objects that are not mentioned above can be clearly understood by those skilled in the art from the following description.

Solution to Problem

Hereinafter, various embodiments described herein will be described with reference to figures. In the following description, numerous specific details are set forth, such as specific configurations, compositions, and processes, etc., in order to provide a thorough understanding of the present invention. However, certain embodiments may be practiced without one or more of these specific details, or in combination with other known methods and configurations. In other instances, known processes and preparation techniques have not been described in particular detail in order to not unnecessarily obscure the present invention. Reference throughout this specification to "one embodiment" or "an embodiment" means that a particular feature, configuration, composition, or characteristic described in connection with the embodiment is included in at least one embodiment of the present invention. Thus, the appearances of the phrase "in one embodiment" or "an embodiment" in various places throughout this specification are not necessarily referring to the same embodiment of the present invention. Additionally, the particular features, configurations, compositions, or characteristics may be combined in any suitable manner in one or more embodiments.

Unless otherwise specified in the specification, all the scientific and technical terms used in the specification have the same meanings as commonly understood by those skilled in the technical field to which the present invention pertains.

In an embodiment of the present invention, "prenatal diagnosis" means diagnosing congenital abnormalities before birth, and is also referred to as pre-birth diagnosis or intrauterine diagnosis. Using a fetal or a decidual material from a fetal as a sample, testing is performed by a method using cytogenetics, biochemical analysis and imaging. It aims at the early discovery of congenital abnormalities related to development and the protection of maternity. Techniques include invasive methods (amniocentesis, chorionic villus sampling, fetal blood sampling, fetal skin biopsy, and fetal liver biopsy) and non-invasive methods (ultrasonic testing, fetal cell sampling from pregnant women, etc.).

Genetic prenatal diagnosis is performed when any one or more of parents shows chromosomal abnormalities or severe genetic diseases, or when a pregnant woman is capable of giving birth to an abnormal child, or is a pregnant woman of advanced maternal age, or has fetal poisoning which is checked by ultrasonic testing, or is suspected of having chromosomal abnormalities, single genetic disease, or inherited metabolic disorder, etc. In karyotype analysis, amniocentesis in terms of safety should be performed, and as a rule, blood is sampled between 15 and 18 weeks of pregnancy. For DNA diagnosis, chorionic villus sampling is also performed, in which the chorionic villus is sampled through the vagina or the abdomen between 9 and 11 weeks of pregnancy. Fetal blood is sampled from the umbilical cord through the abdomen after 16 weeks of pregnancy. For cytogenetic diagnosis, karyotype testing is performed by fluorescence in situ hybridization (FISH) to cultured fetal cells, and for molecular genetic diagnosis, direct diagnosis is performed by Southern blotting or polymerase chain reaction (PCR), or indirect diagnosis is performed by restriction fragment length polymorphism (RFLP) or PCR-RFLP techniques, etc.

In an embodiment of the present invention, the term "chromosomal aneuploidy" is also referred to as "chromosomal heteroploidy", and means a state in which the number of chromosomes per cell in cells, individuals or populations is not an integral multiple of the basic number, but is greater or smaller than the integral multiple by 1 or several digits, that is, a state in which a genome with an incomplete structure is included. A cell or an individual, which is in this state, is referred to as aneuploid (or heteroploid). Generally, the case in which the number of chromosomes is greater than an integral multiple of the basic number is referred to as hyperploidy, and the case in which the number of chromosomes is smaller than an integral multiple of the basic number is referred to as hypoploidy. Particularly, for diploids, the case in which a pair of two homologous chromosomes is deleted is referred to as nullisomy, and the case in which one homologous chromosome is deleted while the other homologous chromosome exists is referred to as monosomy, and the case in which another extra chromosome exists in addition to a pair of homologous chromosomes is referred to as trisomy.

The common trisomy of sex chromosomes is XXY, and is Klinefelter's syndrome characterized mainly by testicular dysfunction. In addition, there are Turner's syndrome in which the number of X chromosomes is 1 (XO) and the ovary does not develop, and XXX females in which the number of X chromosomes is 3, and YY syndrome (YY males) with XYY. Typical trisomy disorders include, but are not limited to, Down's syndrome in which chromosome 21 is trisomic, Edward's syndrome in which chromosome 18 is trisomic and which causes developmental disorder in the fetal period, and Patau's syndrome in which chromosome 13 is trisomic and which involves severe malformation. Cat's cry syndrome refers to a disorder having the peculiarity of a characteristic crying sound and is caused by partial deletion of the short arm of chromosome 5.

In an embodiment of the present invention, "real-time polymerase chain reaction (real-time PCR)" is also referred to as quantitative real time polymerase chain reaction (qPCR), and is a molecular biological experimental technique that amplifies a target DNA molecule and, at the same time, measures the amount of the target DNA molecule. RT-PCR that is generally used refers to a reverse transcription polymerase chain reaction, and is not real-time PCR. However, those skilled in the art do not name it with clear discrimination. Real time PCR can detect the absolute copy number or relative amount of one or more genes having a specific sequence in a DNA sample.

An experiment is performed according to general PCR. An important characteristic is that amplified DNA is measured in real time. This is a difference from basic PCR in which DNA is observed in a final stage. Two general methods are used in the real time PCR: (1) a non-specific fluorescent stain that can enter any DNA double helix; and (2) a sequence-specific DNA probe consisting of an oligonucleotide. A reporter is labeled with fluorescence, and is detected after binding to a complementary DNA target. Often, real time PCR is performed in combination with reverse transcription PCR in order to measure the amount of non-coding RNA not coded by the mRNA of cells or tissue.

In an embodiment of the present invention, "digital polymerase chain reaction (digital PCR)" is a new approach for detecting and quantifying nucleic acids, and enables accurate quantitative analysis and the highly sensitive detection of a target nucleic acid molecule, compared to conventional qPCR. A method for analyzing the results of conventional qPCR is an analog method, whereas the digital PCR method whose results are analyzed by a digital method (because the resultant signal has a value of "0" or "1") has advantages in that it can analyze a large volume of a sample, can test various samples at the same time, and can perform various tests at the same time. The digital PCR technique is a technique that can absolutely quantify a DNA sample using a single molecule counting method without a standard curve, and can perform more accurate absolute quantification by PCR for a single droplet per well (see Gudrun Pohl and le-Ming Shih, Principle and applications of digital PCR, Expert Rev. Mol. Diagn. 4(1), 41-47 (2004)).

In digital PCR, each droplet comprising a sample gene template prepared so as to be diluted to an average copy number of 0.5-1, amplification primers and a fluorescent probe, is dispensed into a single well, and emulsion PCR is performed. Then, a well showing a fluorescent signal is counted as a value of "1", because a sample having a gene copy number of 1 is dispensed into the well and shows the signal after amplification, and a well showing no signal is counted as "0", because a sample having a copy number of 0 is dispensed into the well and shows no signal due to no amplification. In this way, absolute quantification can be achieved.

In digital PCR, the reliability of data is guaranteed only when the gene copy number per well showing a fluorescent signal is 1. In quantification in digital PCR, if the signal per well appears or does not appear in the Poisson distribution, it is considered a digital value of 1 or 0, and the ratio of the positive value (1) to the negative value (0) is calculated. If the ratio of the positive value to the sum of the positive value and the negative value greatly deviates from a gene copy number of 1 in the Poisson distribution, it probably means that the gene copy number per well is greater than 1. Thus, in this case, the reliability of data cannot be guaranteed. For this reason, in digital PCR, the value quantified after amplification does not satisfy the Poisson distribution. Thus, if the gene copy number per well is very greater than 1, it is important to dilute a gene sample so as to satisfy the Poisson distribution. If the gene copy number per well approaches 1, it is important to correct the value (for example, correction may be performed using the Poisson9 program).

However, in the digital PCR method, a technology for correction of quantitative analysis to ensure the data reliability of digital PCR has been required to date, despite the easiness of quantitative analysis, high-throughput analysis, the ability to process a large amount of samples, etc., and there is technical difficulty in adjusting the gene copy number per well to 1. Particularly, as described above, when is performed and digital PCR on chromosomal numerical abnormalities is performed using a primer pair specific for a target gene and a probe in order to perform gene analysis on abnormalities in the number of fetal genes from pregnant woman's blood or plasma, there is a problem in that, due to the background signal of a large amount of pregnant woman's genes, abnormalities in the number of chromosomes associated with a small amount of fetal target gene present in the pregnant woman's blood or plasma are not detected or are detected as unclear signals. This problem becomes a barrier that makes it difficult to combine a genotype analysis technique utilizing fetal cell-free genes with a digital PCR technique.

Thus, there is a need to provide a technology that shows reliable quantitative results by satisfying the Poisson distribution required for digital PCR technology while overcoming the problem in that it is difficult to separate only signals derived from fetal genes and the problem caused by the background signal of pregnant woman's genes, when analyzing fetal numerical chromosomal abnormalities based on the digital PCR technology by use of a very small amount of fetal genes present in pregnant woman's blood or plasma.

In an embodiment of the present invention, "control gene" refers to a normal gene that is used as a test reference to determine whether or not a target gene is abnormal. For example, a control gene, as used herein, is a gene a known to be not associated with chromosomal aneuploidy in a pregnant woman's chromosome set or a fetal chromosome set from pregnant woman' blood or plasma, and may be a gene on chromosome 1 or chromosome 2, but is not limited thereto.

In an embodiment of the present invention, "target gene" is a gene having a mutation useful for genotype analysis, among genes in a sample to be analyzed. Examples of the target gene include marker genes that are used for genetic typing or individual identification, marker genes that are used for diagnosis of specific diseases, genes associated with chromosomal numerical abnormalities or genetic abnormalities, genes having genetically significant mutations, genes having STR (short tandem repeat), and genes having a single nucleotide polymorphism. For example, the target gene that is used herein is a gene a known to be associated with chromosomal aneuploidy, and may be a gene on chromosome 21 (Down's syndrome), chromosome 18 (Edward's syndrome) or chromosome 13 (Patau's syndrome), but is not limited thereto.

In an embodiment of the present invention, "diagnosis" means confirming the presence or feature of pathology. For the purpose of the present invention, diagnosis means analyzing fetal genetic information from pregnant woman's blood to determine whether or not the number of chromosomes is abnormal.

In an embodiment, the present invention provides a method for providing information for diagnosis of chromosomal aneuploidy in a fetus, the method comprising the steps of: (a) extracting DNAs from pregnant woman's blood; (b) classifying the DNAs according to size to obtain DNAs having a size of 1,000 bp or less; (c) performing digital PCR using the obtained DNAs of step (b), for a control gene located on a chromosome not associated with chromosomal aneuploidy and a target gene located on a chromosome associated with chromosomal aneuploidy; (d) calculating the ratio of the quantitative digital PCR value of the target gene to the quantitative digital PCR value of the control gene; and (e) determining that when the ratio calculated in step (d) is 0.70-1.14, the chromosome number of the fetus is normal. The method for providing information for diagnosis of chromosomal aneuploidy in a fetus according to the present invention comprises a step of determining that when the ratio calculated in step (d) is 0.95-1.10, the chromosome number of the fetus is normal. In the method for providing information for diagnosis of chromosomal aneuploidy in a fetus according to the present invention, step (b) of classifying the DNAs according to size comprises the steps of: (a) adding first magnetic beads (bead A) to the DNAs and recovering DNAs not bound to bead A; and (b) adding second magnetic beads (bead B) to the recovered DNAs and eluting a DNA bound to bead B, wherein each of bead A or bead B is added to the DNAs at a ratio of 0.75 to 1.25:1 (Bead A or Bead B:DNAs). In the method for providing information for diagnosis of chromosomal aneuploidy in a fetus according to the present invention, each of bead A or bead B is added to the DNAs at a ratio of 0.75-1.0:1 (Bead A or Bead B:DNAs).

In another embodiment, the present invention provides a method for providing information for diagnosis of chromosomal aneuploidy in a fetus, the method comprising the steps of: (a) extracting DNAs from pregnant woman's blood; (b) classifying the DNAs according to size to obtain DNAs having a size of 1,000 bp or less; (c) performing digital PCR using the obtained DNAs of step (b), for a control gene located on a chromosome not associated with chromosomal aneuploidy and a target gene located on a chromosome associated with chromosomal aneuploidy; (d) calculating the ratio of the quantitative digital PCR value of the target gene to the quantitative digital PCR value of the control gene; and (e) determining that when the ratio calculated in step (d) is 0.10-0.69, or 1.15-1.80, the chromosome number of the fetus is abnormal. The method for providing information for diagnosis of chromosomal aneuploidy in a fetus comprises a step of determining that when the ratio calculated in step (d) is 0.45-0.69, or 1.15-1.31, the chromosome number of the fetus is abnormal. The method for providing information for diagnosis of chromosomal aneuploidy in a fetus comprises a step of determining that when the ratio calculated in step (d) is 0.10-0.69, the fetus has monosomy. In the method according to the present invention, the monosomy is Turner's syndrome. The method according to the present invention comprises a step of determining that when the ratio calculated in step (d) is 1.15-1.80, the fetus has trisomy. In the method according to the present invention, the trisomy is Down's syndrome, Edward's syndrome, or Patau's syndrome. In the method according to the present invention, step (b) of classifying the DNAs according to size comprises the steps of: (a) adding first magnetic beads (bead A) to the DNAs and recovering DNAs not bound to bead A; and (b) adding second magnetic beads (bead B) to the recovered DNAs and eluting a DNA bound to bead B, wherein each of bead A or bead B is added at a ratio of 0.75 to 1.25:1 (Bead A or Bead B:DNAs). In the method for providing information for diagnosis of chromosomal aneuploidy in a fetus according to the present invention, each of bead A or bead B is added to the DNAs at a ratio of 0.75-1.0:1 (Bead A or Bead B:DNAs).

In addition, in the above-described method for providing information for diagnosis of chromosomal aneuploidy in a fetus, the target gene may be any one or more selected from the group consisting of genes having nucleotide sequences of SEQ ID NOs: 1 to 4. In the method according to the present invention, a pair of primers of SEQ ID NOs: 7 and 8 is used as a primer pair for amplifying the target gene having the nucleotide sequence of SEQ ID NO: 1, and an oligonucleotide of SEQ ID NO: 9 is used as a probe for detecting an amplification product of the target gene having the nucleotide sequence of SEQ ID NO: 1. Moreover, a pair of primers of SEQ ID NOs: 10 and 11 is used as a primer pair for amplifying the target gene having the nucleotide sequence of SEQ ID NO: 2, and an oligonucleotide of SEQ ID NO: 12 is used as a probe for detecting an amplification product of the target gene having the nucleotide sequence of SEQ ID NO: 2. Furthermore, a pair of primers of SEQ ID NOs: 13 and 14 is used as a primer pair for amplifying the target gene having the nucleotide sequence of SEQ ID NO: 3, and an oligonucleotide of SEQ ID NO: 15 is used as a probe for detecting an amplification product of the target gene having the nucleotide sequence of SEQ ID NO: 3. In addition, a pair of primers of SEQ ID NOs: 16 and 17 is used as a primer pair for amplifying the target gene having the nucleotide sequence of SEQ ID NO: 4, and an oligonucleotide of SEQ ID NO: 18 is used as a probe for detecting an amplification product of the target gene having the nucleotide sequence of SEQ ID NO: 4.

In addition, in the above-described method for providing information for diagnosis of chromosomal aneuploidy in a fetus, the control gene may be any one or more selected from the group consisting of genes having nucleotide sequences of SEQ ID NOs: 5 and 6. In the method according to the present invention, a pair of primers of SEQ ID NOs: 19 and 20 is used as a primer pair for amplifying the control gene having the nucleotide sequence of SEQ ID NO: 5, and an oligonucleotide of SEQ ID NO: 21 is used as a probe for detecting an amplification product of the control gene having the nucleotide sequence of SEQ ID NO: 5. Furthermore, a pair of primers of SEQ ID NOs: 22 and 23 is used as a primer pair for amplifying the control gene having the nucleotide sequence of SEQ ID NO: 6, and an oligonucleotide of SEQ ID NO: 24 is used as a probe for detecting an amplification product of the control gene having the nucleotide sequence of SEQ ID NO: 6.

Hereinafter, each step of the method according to the present invention will be described in detail.

Advantageous Effects of Invention

The present invention has been made in order to solve the above-described problems occurring in the prior art, and is intended to a method capable of increasing the accuracy of analysis of fetal genetic information by concentrating fetal DNA when prenatal diagnosis is performed using pregnant woman's blood. The prenatal diagnosis method of the present invention is safe for all pregnant women and fetuses, convenient, accurate and reliable, and thus is expected to be highly useful in the prenatal diagnosis field.

BRIEF DESCRIPTION OF DRAWINGS

FIG. 2 shows the results obtained by performing digital PCR on normal or Down's syndrome cells and normalizing the quantitative digital PCR value of a target gene relative to the quantitative digital PCR value of a control gene.

FIG. 3 shows the results obtained by performing digital PCR on amniotic fluid samples from pregnant women, who conceived normal or Down's syndrome fetuses, and normalizing the quantitative digital PCR value of a target gene relative to the quantitative digital PCR value of a control gene.

FIG. 4 shows the results obtained by classifying DNAs according to fragmented particle size for a DNA sample consisting of a 1:1 mixture of long DNA (LD) and short DNA (SD), and analyzing how LD is removed according to the amount of a first bead (bead A) added to the DNA sample.

FIG. 5 shows the results obtained by quantifying the ratio of fetal DNA and pregnant women's DNA from a pregnant woman's blood sample by use of APP gene.

FIG. 6 shows the results obtained by performing digital PCR on gDNA samples comprising normal gDNA and Down syndrome gDNA, mixed at various ratios, and calculating the ratio of the Down syndrome gene to the normal gene.

FIG. 7 shows the results obtained by extracting cfDNAs from the plasma of a pregnant woman who conceived a normal or Down syndrome fetus (T21), classifying the extracted DNAs according to fragmented particle size, performing digital PCR on the DNAs, and normalizing the quantitative digital PCR value of a target gene relative to the quantitative digital PCR value of a control gene.

BEST MODE FOR CARRYING OUT THE INVENTION

Figure 1:
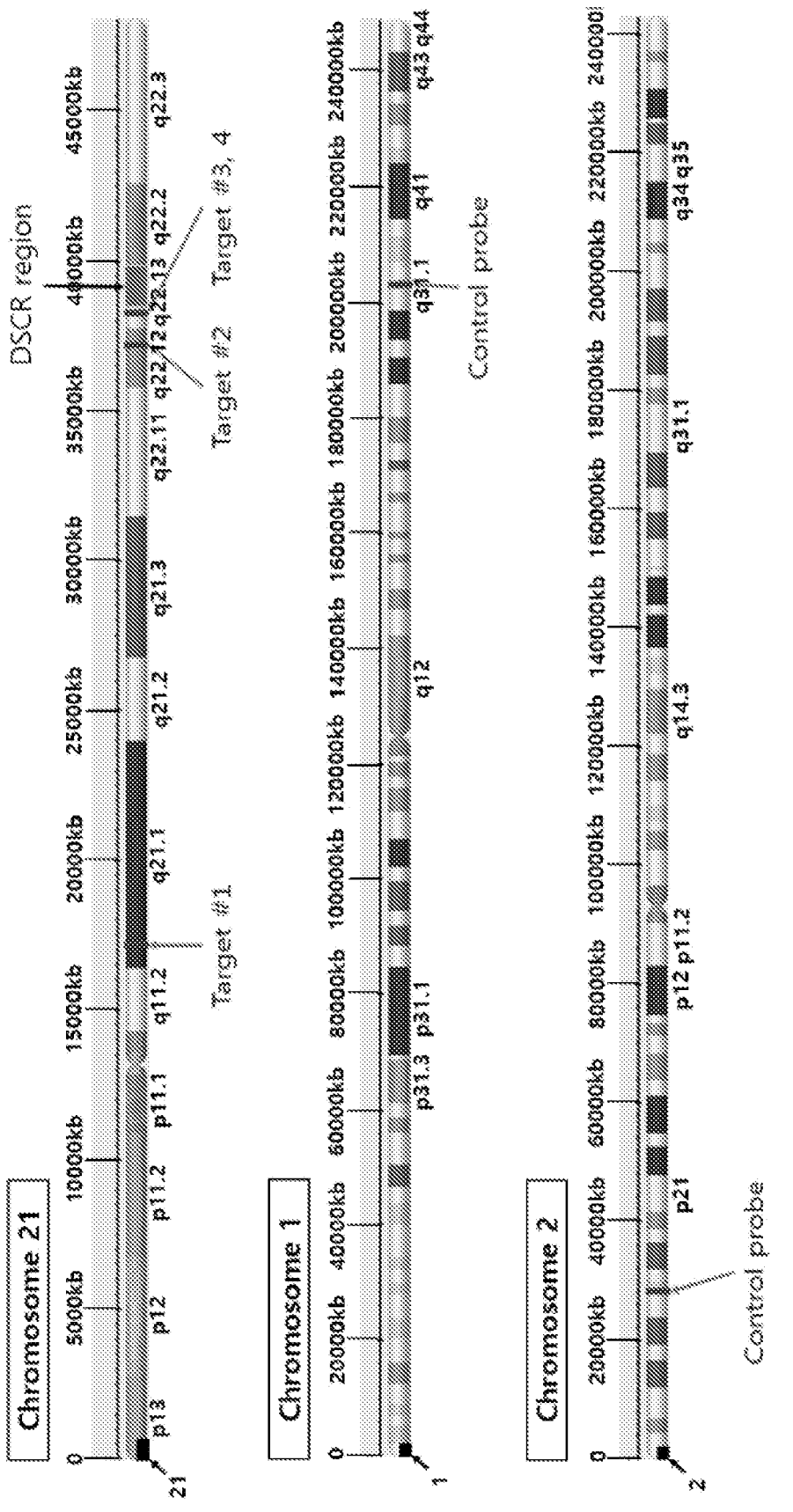
FIG. 1 shows the locus of a target gene or a control gene on each of chromosomes 21, 1 and 2.

There is provided a method for diagnosis of chromosomal aneuploidy in a fetus, the method comprising the steps of: extracting DNAs from pregnant woman's blood; classifying the DNAs according to size to obtain DNAs having a size of 1,000 bp or less; performing digital PCR using the obtained DNAs of step (b), for a control gene located on a chromosome not associated with chromosomal aneuploidy and a target gene located on a chromosome associated with chromosomal aneuploidy; calculating a ratio of a quantitative digital PCR value of the target gene to a quantitative digital PCR value of the control gene; and determining that when the ratio calculated in 0.70-1.14, a chromosome number of the fetus is normal.

MODE FOR THE INVENTION

Hereinafter, the present invention will be described in further detail. It will be obvious to those skilled in the art that these examples are for illustrative purposes only and are not intended to limit the scope of the present invention.

Example 1: Selection of Control Gene and Target Gene and Design of Primer Pair and Probe In order to perform genetic analysis of fetal genes, for example, analysis of numerical chromosomal abnormalities such as trisomy, chromosome 21 (causing Down's syndrome upon trisomy) was selected as a target chromosome, and chromosome 1 and chromosome 2 were selected as control chromosomes. Then, for gene detection, the genes of four regions on chromosome 21 were selected as target genes, and the gene of one region on chromosome 1 and the gene of one region on chromosome 2 were selected as control genes. Based on these genes, a primer pair for amplifying each gene and a fluorescence-labeled probe capable of confirming an amplification reaction product were designed. These primers and probes were synthesized by Bioneer Co., Ltd. (Daejeon, Korea) and Thermo Fisher Scientific (USA), respectively. The selected regions on chromosomes 21, 1 and 2 are shown in FIG. 1, and the sequences and design of the above-mentioned primer pairs and probes are shown in Tables 1 and 2 below.

TABLE 1

| SEQ ID NO: | Gene | Chromosome | Gene locus | Nucleotide sequence(5'-3') |
|---|---|---|---|---|
| SEQ ID NO: 1 | Target gene 1 | 21 | 36616417-36616581 | CTGCAGTTCTTTGTGAACACTCTCATTTGTTGTATCTGTAGGCTGTCTCTCTCAGTGGTAAATGCCTTCGTGTGTTTGTAATGCTGATGGTTACTTGAGGTAAATAAGAATGTACCACTTGGCTCAGTGTGCATGATGTAAGCTTGTCTTTGTTGTATGTTGGCT |
| SEQ ID NO: 2 | Target gene 2 | 21 | 36071971-36072131 | TGACTATCACATGTCTTTGGTTGTAAACTGCTGTGATAGTTACCCTAAGTAATGGGACAGGAGATGAACCCACCCATTAAATAACACAGCAATTAAGCAGCCACTTTTAGAAAAATTTAAATGTGTGGCTTCGAGTTGGGTACTTGCATGTACAGCTTACT |
| SEQ ID NO: 3 | Target gene 3 | 21 | 44773359-44773476 | CCCAGGCTATGCTAGAAGGTATGCTTACAATTGGAAAGTGTAGGCAGATAACATTAAATGGCAATAGCATGTGTAAACTAACTGCAAATGAGGAAAAGGACATTCTAAAGACAGGAT |
| SEQ ID NO: 4 | Target gene 4 | 21 | 36465317-36465426 | GGACCAGAGGTTTATTGGAGGTCTAAATATTTATGGAGAGCAATGATGGCTAATTTTAGAAACCATTAGGTTGCTATTTTAAACGTGTGCTATAAGGATTGCTAATTT |
| SEQ ID NO: 5 | Control gene 1 | 1 | 202879715-202879841 | GAGGAAGCAACTAGAAAACAATGGAAGGGACTTCAGATGGTAAGGTTTCTGTTTAGTACTTATTTCAATTTTAGGCCTCCTGAATAGTAGAGGTGGTGACAGGAGGATACCTGAAACCTTGGTTATA |
| SEQ ID NO: 6 | Control gene 2 | 2 | 28398885-28398996 | GGGAACATCCCAGGTTCAGTAAAAATACAGAGTATTTGCGTTAAACTGGACCTCAGTGGGATGTGATGGGAGGTATGAGACAGATTGTGCCCTTATCCTTTTCTCTTCTTG |

TABLE 2

| | Forward primer (5'-3') | Reverse primer (5'-3') | Fluorescent probe (5'-3') |
|---|---|---|---|
| SEQ ID NO: 1 | (SEQ ID NO: 7) CGTGTGTTTGTAATGCTGATGGT | (SEQ ID NO: 8) CATCATGCACACTGAGCCAAGT | (SEQ ID NO: 9) ACTTGAGGTAAATAAGAATGTAC(5'-VIC, 3'-MGB_NFQ) |
| SEQ ID NO: 2 | (SEQ ID NO: 10) CCCTAAGTAATGGGACAGGAGATG | (SEQ ID NO: 11) AAGTGGCTGCTTAATTGCTGTGT | (SEQ ID NO: 12) ACCCACCCATTAAAT(5'-VIC, 3'-MGB_NFQ) |
| SEQ ID NO: 3 | (SEQ ID NO: 13) TGCTAGAAGGTATGCTTACAATTGGA | (SEQ ID NO: 14) TCATTTGCAGTTAGTTTACACATGCT | (SEQ ID NO: 15) AAGTGTAGGCAGATAAC(5'-VIC, 3'-MGB_NFQ) |
| SEQ ID NO: 4 | (SEQ ID NO: 16) GACCAGAGGTTTATTGGAGGTCTAAAT | (SEQ ID NO: 17) CACGTTTAAAAATAGCAACCTAATGG | (SEQ ID NO: 18) TTTATGGAGAGCAATGAT(5'-VIC, 3'-MGB_NFQ) |
| SEQ ID NO: 5 | (SEQ ID NO: 19) CAACTAGAAAACAATGGAAGGGACTT | (SEQ ID NO: 20) TCAGGAGGCCTAAAATTGAAATAAG | (SEQ ID NO: 21) AGATGGTAAGGTTTCTGTTTAG(5'-FAM, 3'-MGB_NFQ) |

TABLE 2-continued

| | Forward primer (5'-3') | Reverse primer (5'-3') | Fluorescent probe (5'-3') |
|---|---|---|---|
| SEQ ID NO: 6 | (SEQ ID NO: 22) CATCCCAGGTTC AGTAAAAATACAGA | (SEQ ID NO: 23) CTGTCTCATACCTC CCATCACATC | (SEQ ID NO: 24) TATTTGCGTTAA ACTGGACC(5'-FAM, 3'-MGB_NFQ) |

Example 2: Digital PCR for Normal or Down Syndrome Cells

In order to obtain digital PCR result values for normal or Down syndrome (T21) gDNA, normal or Down syndrome (T21) gDNA was purchased from Coriell.

Using the gDNA as a template, digital PCR was performed using a QX200 digital PCR system (Bio-Rad, USA). To establish the suitable concentration of a sample for digital PCR, a gDNA sample was serially diluted 1-5000 folds in an experiment. As a master mix for digital PCR, 20 μl of a reaction solution, containing 0.5-1.0 μM of primers and 0.1-0.25 μM of a probe and adjusted to a sample injection concentration of 2-10 ng, was prepared (see Table 3 below), and dispensed into each PCR tube. The PCR tubes containing the solution were mounted in DG8 droplet generator cartridges, and then 20 μl of a sample was dispensed into a sample well, and 70 μl of droplet generator oil (Gasket) was dispensed into an oil well. Next, a gasket was mounted in the cartridge, and then a droplet generation reaction was performed using a QX200 droplet generator. The generated droplets were dispensed onto a 96-well PCR plate, and then PCR was performed under the temperature conditions shown in Table 4 below.

TABLE 3

| No. | PCR amplification composition | Volume (μl) |
|---|---|---|
| 1 | Sample having DNA template | 1 |
| 2 | Primer/probe set | 9 |
| 3 | ddPCR Supermix for probes | 10 |
| | Sum | 20 |

TABLE 4

| No. | Step | Temperature | Time | Cycles |
|---|---|---|---|---|
| 1 | Pretreatment | 95° C. | 10 min | |
| 2 | Denaturation | 94° C. | 30 sec | 40 cycles |
| 3 | Annealing | 60° C. | 60 sec | |
| 4 | Hold | 98° C. | 10 min | |

After completion of the reaction, each well was mounted on a QX200 droplet reader, and the value of copies/μl for each probe was analyzed. Using the value of copies/μl for each probe, the quantitative digital PCR values of target genes (SEQ ID NOs: 1 to 4), normalized relative to the quantitative digital PCR value of each control gene (SEQ ID NO: 5 or 6), were calculated. The results are shown in FIG. 2.

The experimental results indicated that the calculated ratio values for normal somatic cell samples (n=4) were 1.1714, 1.0256, 1.0821 and 1.0255, respectively, and the average value thereof was 1.08, and that the calculated ratio values for Down syndrome (T21) somatic cell samples (n=4) were 2.1000, 1.4388, 1.3611 and 1.1387, respectively, and the average value thereof was 1.51. Thus, it could be seen that the calculated ratio for the Down syndrome samples was about 1.5 times that for the normal samples.

Example 3: Digital PCR for Amniotic Fluid Samples of Pregnant Women Who Conceived Normal or Down Syndrome Fetus Fetal cfDNA was extracted from amniotic fluid samples of pregnant women who conceived a normal or Down syndrome (T21) fetus. Using the fetal cfDNA as a template sample, digital PCR was performed.

First, using a QIAamp Circulating Nucleic Acid Kit (Qiagen Cat #55114, QIAGEN, Germany), gDNA was extracted from cells. gDNA extraction was performed according to the manufacturer's manual. Specifically, cells were lysed with protein lysate buffer, and 100 μl of proteinase K was added to a 50 ml centrifugation tube in order to remove protein components to thereby increase the purity of a sample. Then, to the 50 ml centrifugation tube containing proteinase K, ACL buffer containing 1.0 μg of carrier RNA, followed by vortexing to mix the cell lysate with the ACL buffer. The mixture was incubated at 60° C. for 30 minutes, and then 3.6 ml of ACB buffer (lysate buffer) was added to the centrifugation tube, followed by vortexing to obtain an ACB buffer mixture which was then incubated on ice for 5 minutes.

To increase the yield of extracted gDNA by increasing the adsorption ability of a membrane present on a column of a QIAamp circulating nucleic acid kit, a vacuum pump system was used. Using the vacuum pump system, the ACB buffer mixture was allowed to flow to the QIAamp Mini column equipped with a 20 ml tube extender. After the vacuum pump system was operated to allow the ACB buffer mixture to flow, the value of the vacuum pump system was adjusted to 0, and the tube extender was removed. Through this procedure, the largest possible amount of the reaction material was bound to the membrane of the QIAamp Mini column. Thereafter, 600 μl of ACW1 buffer that is a first buffer solution for washing the reaction material bound to the QIAamp Mini column was allowed to flow to the QIAamp Mini column by operation of the vacuum pump system, and then the value of the vacuum pump system was adjusted to 0, and the tube extender was removed. Through this procedure, DNA bound to the QIAamp Mini column was washed. In addition, a second washing operation was performed to obtain highly pure DNA. 750 μl of ACW2 buffer that is a second washing solution was allowed to flow to the QIAamp Mini column by operation of the vacuum pump system, and then the value of the vacuum pump system was adjusted to 0, and the tube extender was removed. Through this procedure, DNA bound to the QIAamp Mini column was additionally washed, thereby obtaining highly pure DNA.

750 μl of ethanol (96 to 100%) that is a final washing solution was allowed to flow to the QIAamp Mini column by operation of the vacuum pump system, and then the value of the vacuum pump system was adjusted to 0, and the tube extender was removed. Furthermore, the ethanol component was removed to the greatest possible extent by drying to thereby increase the purity of extracted DNA, and then the QIAamp Mini column was closed, flowed by centrifugation at 20,000 g and 14,000 rpm for 3 minutes. The QIAamp Mini column was opened, followed by drying at 56° C. for 10 minutes. Thereafter, 20 µl of AVE buffer was added to the QIAamp Mini column, followed by incubation at room temperature for 3 minutes, after which the QIAamp Mini column was closed, followed by centrifugation at 20,000 g and 14,000 rpm for 1 minute. Thus, each corresponding cfDNA sample was obtained from normal or Down syndrome (T21) somatic cells.

Digital sample for each sample was performed according to the same method under the same conditions as described in Example 2. The results are shown in FIG. 3.

The experimental results indicated that the calculated ratio values for the amniotic samples (n=4) of pregnant women who conceived a normal fetus were 1.1991, 1.0574, 1.0006 and 0.9560, respectively, and the average value thereof was 1.05, and that the calculated ratio values for the amniotic samples (n=4) of pregnant women who conceived a Down syndrome (T21) fetus were 1.6584, 1.6954, 1.4886 and 1.5062, respectively, and the average value thereof 1.59. Thus, it could be seen that the calculated ratio for the Down syndrome samples was about 1.5 times that for the normal samples, and this result value was similar to the result value of the experiment performed using the normal or Down syndrome cells as the sample.

Example 4: Confirmation of Classification of DNAs According to Fragmented Particle Size at Various Ratios of SPRIselsect Magnetic Beads Because fetal DNA is smaller in size than pregnant woman's DNA, a method of extracting cfDNA according to the DNA length was selected in order to increase the reflection rate of information about fetal cfDNA showing a short length (bp). To construct DNAs having different sizes, gDNAs were fragmented under two conditions (long and short lengths; 5 and 15 minutes) by use of Ion Shear™ Plus Reagents Kit (Cat #4471252, Thermo Fisher Scientific) according to the manufacturer's manual. Classification of gDNAs according to fragmented particle size was performed using a SPRIselsect kit (Beckman Coulter, Germany) according to the manufacturer's manual. This will now be described in detail.

First, a gDNA-containing sample and magnetic beads (named "bead A") were mixed with each other so that long DNAs (LD) would first be adsorbed onto the beads. Following this, the beads were separated using a magnet, and then DNAs remaining in the supernatant without being adsorbed onto the beads were transferred into a fresh tube, and fresh beads (named "bead B") were added to the tube to extract the remaining DNAs (short DNAs (SD)). The adsorbed DNAs were extracted from bead A and bead B in the respective tubes.

On a DNA sample comprising LD and SD, mixed at a ratio of 1:1 according to the above-described method, how LD was removed according to the amount of bead A added to the DNA sample was analyzed. The results of the analysis are shown in FIG. 4.

The experimental results indicated that, when bead A was added in an amount equal to 0.5 times of DNA sample, bead A and bead B all had no effect on the discrimination of the size of DNAs. However, it could be seen that, when bead A was added in an amount equal to 0.75 times of DNA sample, bead A adsorbed DNAs having a length of 400 bp or more, and bead B adsorbed DNAs having a length of 500 bp or less, and when bead A was added in an amount equal to 1.0 time of DNA sample, bead A adsorbed DNAs having a length of 200 bp or more, and bead B adsorbed DNAs having a length of 300 bp or less, and when bead A was added in an amount equal to 1.25 times of DNA sample, bead A adsorbed DNAs having a length of 150 bp or more, and bead B adsorbed DNAs having a length of 200 bp. This suggests that as the amount of bead A added increase, the amount of LD removed also increases. Considering that the length of fetal cfDNAs is about 150 bp or less, it was determined that the ratio of bead A, added to the DNA sample for concentrate fetal cfDNAs, is preferably 0.75-1.25, more preferably 0.75-1.0 times of DNA sample.

Example 5: Quantification of Ratio of Fetal DNA and Pregnant Woman's DNA from Pregnant Woman's Blood Sample It is known that fetal DNA in pregnant woman's blood or plasma is smaller in size than pregnant woman's DNA. Thus, when fetal DNA having a relatively small size and pregnant woman's DNA having a relatively large size are amplified by real-time PCR in connection with a specific gene, the fetal DNA and the pregnant woman's DNA, which are present in pregnant woman's blood or plasma in connection with the specific gene, can be quantified, and the ratio of the amounts of these genes can be calculated.

Thus, in this Example, APP (amyloid precursor protein) gene (GenBank accession No. NM_000484) and β-actin gene were specific genes present commonly in fetal DNA and pregnant women's DNA in pregnant woman's blood or plasma. In addition, primer pairs capable of amplifying fetal DNA and pregnant woman's DNA, associated with the APP gene and the β-actin gene, and fluorescence-labeled probes capable of confirming amplification reaction products, were designed (see Table 5 below).

TABLE 5

| Target gene | Amplicon length | Forward primer (5'-3') | Reverse primer (5'-3') | Fluorescent probe(5'-3') (5'-FAM, 3'-TAMRA) |
|---|---|---|---|---|
| APP | 6 7 bp | TCAGGTTGACGCCGCTGT(SEQ ID NO: 25) | TTCGTAGCCGTTCTGCTGC (SEQ ID NO: 26) | ACCCCAGAGGAGCGCCACCTG(SEQ ID NO: 28) |
| | 180 bp | | TCTATAAATGGACACCGATGGGTAGT(SEQ ID NO: 27) | |

TABLE 5-continued

| Target gene | Amplicon length | Forward primer (5'-3') | Reverse primer (5'-3') | Fluorescent probe(5'-3') (5'-FAM, 3'-TAMRA) |
|---|---|---|---|---|
| β-actin | 83 bp | TACAGGAAGTC CCTTGCCAT(SEQ ID NO: 29) | CCTGTGTGGACTT GGGAGAG(SEQ ID NO: 30) | CCCACTTCTCTCT AAGGAGAATGGC CC (SEQ ID NO: 32) |
| | 170 bp | | CACGAAGGCTCA TCATTCAA(SEQ ID NO: 31) | |
| | 67 bp | AGAGCTACGA GCTGCCTGAC (SEQ ID NO: 33) | CCATCTCTTGCTC GAAGTCC(SEQ ID NO: 34) | TTCCGCTGCCCTG AGGCACT(SEQ ID NO: 36) |
| | 169 bp | | GGCAGGACTTAG CTTCCACA(SEQ ID NO: 35) | |

For reference, in Table 5 above, in order to quantitatively compare fetal DNA with pregnant woman's DNA by real-time PCR to thereby evaluate the ratio of the amounts of these genes, primer pairs were designed in view of the fact that the size of fetal DNA is smaller than the size of pregnant woman's DNA. Particularly, as shown in Table 5 above, in order to accurately evaluate the amount of pregnant woman's gene and the amount of fetal gene and to standardize analysis conditions in quantitative evaluation, detection probes and forward primers for a set of short amplicons from fetal DNA and pregnant woman's DNA and a set of long amplicons from pregnant woman's DNA were designed to be common, and reverse primers were designed to be different. In addition, each detection probe was double-labeled with a fluorescent substance and a quencher substance in order to confirm a real-time PCR amplification product and to quantitatively analyze the PCR amplification product. In this Example, the 5' end of each detection probe was labeled with the fluorescent substance FAM, and the 3' end was labeled with the quencher substance TAMRA.

As shown in Table 5 above, in the case of the APP target gene, a short amplicon (67 bp length) from fetal DNA and pregnant woman's DNA was obtained from a pair of primers of SEQ ID NOs: 25 and 26, and a long amplicon (180 bp length) from pregnant woman's DNA was obtained from a pair of primers of SEQ ID NOs: 25 and 27.

Using the short-length DNA concentration process carried out in this Example, cfDNA was obtained from a pregnant woman who conceived a normal fetus, and real-time PCR was performed to measure the ratio of SD to LD. In this Example, the real-time PCR was performed using a 7900HT Fast Real Time PCR system (Life Technologies, USA).

A real-time PCR composition comprising each primer pair and detection probe for APP gene, a DNA template prepared as described above, and a real-tim
PCR master mixture, was prepared as shown in Table 6 below, and real-time PCR was performed under the real-time PCR conditions shown in Table 7 below. Meanwhile, the PCR master mixture of the PCR amplification composition was composed of, for example, PCR buffer, dNTP, DNA polymerase, etc., and in this Example, TaqMan Universal Master Mix II, no UNG (Life Technologies, Cat. 4440040) was used as the real-time PCR master mixture. Whenever a real-time PCR amplification reaction was repeated once, fluorescence was measured at the FAM wavelength, and the fluorescent intensity for each reaction cycle was analyzed using the SDS software. The results of real-time PCR quantification for the APP gene were summarized for each sample, and the amount of the short amplicon (67 bp length) was divided by the amount of the long amplicon (180 bp length), and are shown in FIG. 5.

TABLE 6

| No. | PCR amplification composition | Volume (μl) |
|---|---|---|
| 1 | Sample having DNA template | 1 |
| 2 | Primer set (forward + reverse) (10 μM) | 1 |
| 3 | Detection probe (5 μM) | 0.5 |
| 4 | Distilled water | 2.5 |
| 5 | TaqMan Universal Master Mix II, no UNG | 5 |
| | Sum | 10 |

TABLE 7

| No. | Step | Temperature | Time | Cycles |
|---|---|---|---|---|
| 1 | Predenaturation | 95° C. | 10 min | |
| 2 | Denaturation | 95° C. | 15 sec | 50 cycles |
| 3 | Annealing | 60° C. | 60 sec | |
| 4 | Extension | 72° C. | 60 sec | |

Example 6: Digital PCR on Sample Comprising Mixture of Normal or Down Syndrome gDNAs Normal gDNA and Down syndrome gDNA were mixed with each other at various ratios to prepare gDNA mixtures. Using each of the gDNA mixtures as a template, digital PCR was performed using the primers and probe shown in Table 2 above, the ratio of the amount of the Down syndrome gene to the amount of the normal gene was calculated. The results of the calculation are shown in FIG. 6.

The experimental results indicated that, as the percentage of Down syndrome gDNA added decreased, the ratio of the amount of the Down syndrome gene to the amount of the normal gene approached 1. In particular, it was shown that, when the reflection rate of information about the Down syndrome gene was as low as less than 10%, the ratio approached a normal value (1.1 or less). Considering that only about 3-13% of cfDNAs present in pregnant woman's blood is generally fetal cfDNAs, it could be seen that cfDNA itself extracted from pregnant woman's blood is used to perform prenatal diagnosis, the accuracy of the diagnosis is very low.

Example 7: Classification of cfDNAs, Extracted from Pregnant Woman's Blood, According to Fragmented Particle Size, and Digital PCR on the cfDNAs cfDNAs were extracted from the plasma of pregnant women, who conceived a normal or Down syndrome (T21) fetus, in the following manner.

First, using MagMAX™ Cell-Free DNA Isolation Kit (Cat #A29319, Thermo Fisher Scientific), cfDNAs were extracted from plasma. cfDNA extraction was performed using 2 mL of plasma according to the manufacturer's manual.

The extracted cfDNAs were classified according to fragmented particle size by the method of Example 4. Using each sample comprising the obtained SD region as a template, digital PCR was performed. From the result values for each sample, the ratio of the target gene to the control gene was calculated. The results of the calculation are shown in FIG. 7.

The experimental results indicated that the calculated ratios for the normal samples (n=3) were 1.04, 1.08 and 0.98, respectively, but the calculated ratios for the Down syndrome samples (n=3) were 1.31 and 1.15 (for two samples), respectively. In the case in which digital PCR is performed using the SD regions obtained by the DNAs according to fragmented particle size, it can be determined that when the calculated ratio of the target gene to the control gene is 0.70-1.14, the chromosome number of the fetus is normal, and more preferably, when the calculated ratio is 0.95-1.10, the chromosome number of the fetus is normal. In addition, it can be determined that when the calculated ratio is 0.10-0.69, or 1.15-1.80, the chromosome number of the fetus is abnormal, and more preferably, when the calculated ratio is 0.45-0.69, or 1.15-1.31, the chromosome number of the fetus is abnormal.

As described above, the method for prenatal diagnosis using digital PCR according to the present invention uses a non-invasive sampling method, and thus is safe for pregnant women and fetuses. Furthermore, the method according to the present invention makes it possible to stably separate the signal of a small amount of a fetal gene from the background signal of a pregnant woman's gene, and thus increases the accuracy of fetal genetic information. Accordingly, it is expected that the method of the present invention will be highly useful for early diagnosis of fetal genetic diseases.

Although the present disclosure has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereof.

INDUSTRIAL APPLICABILITY

The present invention is a method for prenatal diagnosis using digital PCR. In general, amniocentesis is used to diagnose fetal genetic abnormalities. However, amniocentesis is an invasive testing method, can cause various problems, including bacterial infection of the amnion by syringes, wounds caused by syringes, and amniotic fluid leakage, and can also cause abortion in severe cases. The prenatal diagnosis method of the present invention is safe for all pregnant women and fetuses, convenient, accurate and reliable, and thus is expected to be highly useful in the prenatal diagnosis field.

Sequence Listing Free Text

SEQ ID NO: 1 - CTGCAGTTCTTTGTGAACACTCTCATTTGTTGTAT CTGTAG-GCTGTCTCTCTCAGTGGTAAATGCCTTCGTGTGTTTGTAATGC TGATGGTTACTTGAGGTAAATAAGAATGTACCACTTGGCTCAGTGTGCAT GATGTAAGCTTGTCTTTGTTGTATGTTGGCT

SEQ ID NO: 2 - TGACTATCACATGTCTTTGGTTGTAAACTGCTGTG ATAGT-TACCCTAAGTAATGGGACAGGAGATGAACCCACCCATTAAATAA CACAGCAATTAAGCAGCCACTTTTAGAAAAATTTAAATGTGTGGCTTCGA GTTGGGTACTTGCATGTACAGCTTACT

SEQ ID NO: 3 - CCCAGGCTATGCTAGAAGGTATGCTTACAATTG- GAAAAGTGTAGGCAGATAACATTAAATGGCAATAGCATGTGTAAACTAAC TGCAAATGAGGAAAAGGACATTCTAAAGACAGGAT

SEQ ID NO: 4 - GGACCAGAGGTTTATTGGAGGTCTAAATATTTATG GA-GAGCAATGATGGCTAATTTTAGAAACCATTAGGTTGCTATTTTTAAA CGTGTGCTATAAGGATTTGCTAATTT

SEQ ID NO: 5 - AAGGGACTTCAGATGGTAAGGTTTCTGTTTAGTAC T-TATTTCAATTTTAGGCCTCCTGAATAGTAGAGGTGGTGACAGGAGGAT ACCTGAAACCTTGGTTATA

SEQ ID NO: 6 - GGGAACATCCCAGGTTCAGTAAAAATACAGAG- TATTTGCGTTAAACTGGACCTCAGTGGGGATGTGATGGGAGGTATGAGAC AGATTGTGCCCTTATCCTTTTCTCTTCTTG

SEQ ID NO: 7 - CGTGTGTTTGTAATGCTGATGGT

SEQ ID NO: 8 - CATCATGCACACTGAGCCAAGT

SEQ ID NO: 9 - ACTTGAGGTAAATAAGAATGTAC

SEQ ID NO: 10 - CCCTAAGTAATGGGACAGGAGATG

SEQ ID NO: 11 - AAGTGGCTGCTTAATTGCTGTGT

SEQ ID NO: 12 - ACCCACCCATTAAAT

SEQ ID NO: 13 - TGCTAGAAGGTATGCTTACAATTGGA

SEQ ID NO: 14 - TCATTTGCAGTTAGTTTACACATGCT

SEQ ID NO: 15 - AAGTGTAGGCAGATAAC

SEQ ID NO: 16 - GACCAGAGGTTTATTGGAGGTCTAAAT

SEQ ID NO: 17 - CACGTTTAAAAATAGCAACCTAATGG

SEQ ID NO: 18 - TTTATGGAGAGCAATGAT

SEQ ID NO: 19 - CAACTAGAAAACAATGGAAGGGACTT

SEQ ID NO: 20 - TCAGGAGGCCTAAAATTGAAATAAG

SEQ ID NO: 21 - AGATGGTAAGGTTTCTGTTTAG

SEQ ID NO: 22 - CATCCCAGGTTCAGTAAAAATACAGA

SEQ ID NO: 23 - CTGTCTCATACCTCCCATCACATC

SEQ ID NO: 24 - TATTTGCGTTAAACTGGACC

SEQ ID NO: 25 - TCAGGTTGACGCCGCTGT

SEQ ID NO: 26 - TTCGTAGCCGTTCTGCTGC

SEQ ID NO: 27 - TCTATAAATGGACACCGATGGGTAGT

SEQ ID NO: 28 - ACCCCAGAGGAGCGCCACCTG

SEQ ID NO: 29 - TACAGGAAGTCCCTTGCCAT

SEQ ID NO: 30 - CCTGTGTGGACTTGGGAGAG

Sequence Listing Free Text

SEQ ID NO: 31 - CACGAAGGCTCATCATTCAA

SEQ ID NO: 32 - CCCACTTCTCTCTAAGGAGAATGGCCC

SEQ ID NO: 33 - AGAGCTACGAGCTGCCTGAC

Sequence Listing Free Text

SEQ ID NO: 34 - CCATCTCTTGCTCGAAGTCC

SEQ ID NO: 35 - GGCAGGACTTAGCTTCCACA

SEQ ID NO: 36 - TTCCGCTGCCCTGAGGCACT

The invention claimed is:

1. A method for preparing a deoxyribonucleic acid (DNA) fraction from a pregnant human female useful for analyzing a chromosomal aneuploidy in a fetus comprising the steps of:
   (a) extracting DNA molecules from a pregnant woman's blood;
   (b) producing a fraction of the DNA molecules extracted in step (a) having a size of 1,000 bp or less;
   (c) performing digital PCR using the DNA molecules having a size of 1,000 bp or less in step (b) to amplify:
      (i) a target gene located on a chromosome associated with chromosomal aneuploidy wherein the target gene comprises one or more of SEQ ID NO:1, SEQ ID NO:2, SEQ ID NO:3, and SEQ ID NO:4; and
      (ii) a control gene located on a chromosome not associated with chromosomal aneuploidy wherein the control gene comprises one or more of SEQ ID NO:5 and SEQ ID NO:6; and
   (d) calculating a ratio of a quantitative digital PCR value of the target gene to a quantitative digital PCR value of the control gene, and wherein the ratio is calculated by calculating individual ratios with every possible combination of target and control genes and then averaging them.

2. The method of claim 1, wherein when the ratio calculated in step (d) is 0.95-1.10, the chromosome number of the fetus is normal.

3. The method of claim 1, wherein when the ratio calculated in step (d) is 0.10-0.69, or 1.15-1.80, a chromosome number of the fetus is abnormal.

4. The method of claim 1, wherein when the ratio calculated in step (d) is 0.45-0.69, or 1.15-1.31, the chromosome number of the fetus is abnormal.

5. The method of claim 1, wherein when the ratio calculated in step (d) is 0.10-0.69, the fetus has monosomy.

6. The method of claim 5, wherein the monosomy is Turner's syndrome.

7. The method of claim 1, wherein when the ratio calculated in step (d) is 1.15-1.80, the fetus has trisomy.

8. The method of claim 7, wherein the trisomy is Down's syndrome, Edward's syndrome, or Patau's syndrome.

9. The method of claim 1, wherein a pair of primers of SEQ ID NOs: 7 and 8 is used as a primer pair for amplifying the target gene comprising the nucleotide sequence of SEQ ID NO: 1, and an oligonucleotide of SEQ ID NO: 9 is used as a probe for detecting an amplification product of the target gene comprising the nucleotide sequence of SEQ ID NO: 1.

10. The method of claim 1, wherein a pair of primers of SEQ ID NOs: 10 and 11 is used as a primer pair for amplifying the target gene comprising the nucleotide sequence of SEQ ID NO: 2, and an oligonucleotide of SEQ ID NO: 12 is used as a probe for detecting an amplification product of the target gene comprising the nucleotide sequence of SEQ ID NO: 2.

11. The method of claim 1, wherein a pair of primers of SEQ ID NOs: 13 and 14 is used as a primer pair for amplifying the target gene comprising the nucleotide sequence of SEQ ID NO: 3, and an oligonucleotide of SEQ ID NO: 15 is used as a probe for detecting an amplification product of the target gene comprising the nucleotide sequence of SEQ ID NO: 3.

12. The method of claim 1, wherein a pair of primers of SEQ ID NOs: 16 and 17 is used as a primer pair for amplifying the target gene comprising the nucleotide sequence of SEQ ID NO: 4, and an oligonucleotide of SEQ ID NO: 18 is used as a probe for detecting an amplification product of the target gene comprising the nucleotide sequence of SEQ ID NO: 4.

13. The method of claim 1, wherein a pair of primers of SEQ ID NOs: 19 and 20 is used as a primer pair for amplifying the control gene comprising the nucleotide sequence of SEQ ID NO: 5, and an oligonucleotide of SEQ ID NO: 21 is used as a probe for detecting an amplification product of the control gene comprising the nucleotide sequence of SEQ ID NO: 5.

14. The method of claim 1, wherein a pair of primers of SEQ ID NOs: 22 and 23 is used as a primer pair for amplifying the control gene comprising the nucleotide sequence of SEQ ID NO: 6, and an oligonucleotide of SEQ ID NO: 24 is used as a probe for detecting an amplification product of the control gene comprising the nucleotide sequence of SEQ ID NO: 6.

15. The method of claim 1, wherein where the ratio calculated in step (d) is 0.70-1.14, a chromosome number of the fetus is normal.

* * * * *